(12) United States Patent
Morinaka et al.

(10) Patent No.: US 8,815,199 B2
(45) Date of Patent: Aug. 26, 2014

(54) METHOD FOR PRODUCING IMIDE COMPOUND

(75) Inventors: Takayoshi Morinaka, Ube (JP); Tsutomu Nanmyo, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 294 days.

(21) Appl. No.: 13/258,988

(22) PCT Filed: Mar. 29, 2010

(86) PCT No.: PCT/JP2010/055508
§ 371 (c)(1),
(2), (4) Date: Sep. 22, 2011

(87) PCT Pub. No.: WO2010/113835
PCT Pub. Date: Oct. 7, 2010

(65) Prior Publication Data
US 2012/0020867 A1  Jan. 26, 2012

(30) Foreign Application Priority Data

Mar. 31, 2009 (JP) ................................. 2009-085353
Mar. 26, 2010 (JP) ................................. 2010-071231

(51) Int. Cl.
*C07C 209/68* (2006.01)
*C01B 21/086* (2006.01)
*C01B 21/097* (2006.01)

(52) U.S. Cl.
USPC ........... 423/300; 423/301; 423/386; 423/413; 564/463

(58) Field of Classification Search
USPC ........... 423/300, 301, 386, 413, 463; 564/463
See application file for complete search history.

(56) References Cited

U.S. PATENT DOCUMENTS

| | | | |
|---|---|---|---|
| 3,379,509 A | 4/1968 | Appel | |
| 4,315,935 A | 2/1982 | Ali | |
| 5,723,664 A | 3/1998 | Sakaguchi et al. | |
| 6,235,921 B1 | 5/2001 | Kobayashi et al. | |
| 2001/0012903 A1 | 8/2001 | Kobayashi et al. | |
| 2002/0055045 A1* | 5/2002 | Michot et al. | 429/307 |
| 2007/0043231 A1 | 2/2007 | Hammami et al. | |

FOREIGN PATENT DOCUMENTS

| | | |
|---|---|---|
| CN | 1306959 A | 8/2001 |
| EP | 1 029 850 A1 | 8/2000 |
| JP | 6-157563 A | 6/1994 |
| JP | 8-81436 * | 3/1996 |
| JP | 8-217745 A | 8/1996 |
| WO | WO 2007/022624 A1 | 3/2007 |
| WO | WO 2007/104144 A1 | 9/2007 |
| WO | WO 2009/123328 A1 | 10/2009 |

OTHER PUBLICATIONS

European Search Report dated Mar. 8, 2013 (six (6) pages).
Chinese Office Action dated Mar. 18, 2013 (seven (7) pages).
Martin Beran et al., "A New Method of the Preparation of Imido-bis(sulfuric acid) Dihalogenide, (F,Cl), and the Potassium Salt of Imido-bis(sulfuric acid) Difluoride", Z. Anorg Allg. Chem., 2005, vol. 631, No. 1, pp. 55-59.
Corresponding International Search Report with English Translation dated Jun. 8, 2010 (four (4) pages).
Form PCT/ISA/237 (three (3) pages).
Burkhard Krumm et al., "Synthesis of Poly- and the First Perfluoroalkyl-N(SO2F)2 Derivatives: Improved Methods for the Preparation of XN(SO2F)2 (X+H, Cl) and Single-Crystal Diffraction Studies of HN(SO2Cl)2, HN(SO2F)2, and CF3CH2N(SO2F)2", Inorg. Chem. 1998, vol. 37, No. 24, pp. 6295-6303.
John K. Ruff et al., "Imidodisulfuryl Fluoride, Cesium Imidodisulfuryl Fluoride, and Fluoroimidodisulfuryl Fluoride", Inorganic Syntheses, 1968, vol. 11, pp. 138-143.
Kang Xu et al., "A New Protonation Chemistry of Phosphazenes and the Formation of Bis (Sulfonyl) Imides", Inorganic Chemistry Communications, vol. 2, No. 6, Mar. 25, 1999, pp. 261-264, Elsevier.
Von E. Fluck et al., " Bis(difluorphosphoryl)amin Und Einige N-Derivate", Z. Anorg. Allg. Chem., 1975, vol. 412, No. 1, pp. 65-70, J.A. Barth, Leipzig.
Ed. F. Degering et al., "A Potential Industrial Process for Sulfamide", Ind. Eng. Chem., Purdue University, Lafayette, Ind., 1943, pp. 751-753.
W. Traube, "Wilhelm Traube and Emil Reubke: Zur Kenntnis des Sulfamids", Ber., 1923, vol. 56, pp. 1656-1663.

\* cited by examiner

*Primary Examiner* — Wayne Langel

(74) *Attorney, Agent, or Firm* — Crowell & Moring LLP

(57) ABSTRACT

Disclosed is a method for producing "a salt or a complex comprising imide and an organic base", characterized by reacting halogenated sulfuryl or halogenated phosphoryl with ammonia in the presence of an organic base. According to this method, a target imide compound can be produced in a high yield while significantly suppressing the production of by-products. Further, by reacting the obtained imide compound with an alkali metal hydroxide or an alkaline earth metal hydroxide, an imide metal salt can be easily derived.

8 Claims, No Drawings

METHOD FOR PRODUCING IMIDE COMPOUND

TECHNICAL FIELD

The present invention relates to a method for producing: an imide compound useful as an intermediate for medicines and agrichemicals, a battery electrolyte or an acid catalyst; and more specifically, bis(halogenated sulfonyl)imide or a bis (dihalogenated phosphoryl)imide compound.

BACKGROUND OF THE INVENTION

Bis(halogenated sulfonyl)imide or a bis(dihalogenated phosphoryl)imide compound, which has hitherto been known widely, is a substance useful as a solvent for battery electrolytes, an acid catalyst or an ionic liquid, and also as an antistatic agent. As a method for producing a bis(fluorosulfonyl) imide compound, there has been known a production method of Patent Document 1 in which fluorosulfonic acid is reacted with urea thereby obtaining bis(fluorosulfonyl)imide and a production method of Non-Patent Publication 1 in which bis(chlorosulfonyl)imide is reacted with a metal fluoride thereby obtaining bis(fluorosulfonyl)imide.

As a method for producing a bis(chlorosulfonyl)imide compound, there has been known a method of Patent Document 2 in which chlorosulfonic acid ($ClSO_3H$) is reacted with chlorosulfonylisocyanate ($ClSO_2NCO$) thereby obtaining bis (chlorosulfonyl)imide and a method of Non-Patent Document 3 in which chlorosulfonic acid ($ClSO_3H$) is reacted with N-sulfonyl trichlorophosphazene ($ClSO_2NPCl_3$) thereby obtaining bis(chlorosulfonyl)imide.

Relating to a method of producing a bis(difluorophosphoryl)imide compound, there has been known a method of Non-Patent Document 4 in which $LiN(SiMe_3)_2$, a silazane metal compound, is reacted with phosphoryl trifluoride ($POF_3$) thereby obtaining lithium bis(difluorophosphoryl)imide.

As an example of using halogenated sulfuryl used in the invention of the present application, there is disclosed a production method of Non-Patent Documents 5 and 6 where sulfuryl chloride or sulfuryl fluoride is reacted with anhydrous ammonia thereby obtaining sulfamide ($H_2NSO_2NH_2$), and a production method of Patent Document 3 where a tertiary amine such as a silazane derivative is reacted with halogenated sulfuryl thereby obtaining a bis(halogenated sulfonyl)imide derivative.

On the other hand, a production method of reacting halogenated sulfuryl or halogenated phosphoryl with ammonia in the presence of an organic base thereby obtaining bis(halogenated sulfonyl)imide or a bis(halogenated phosphoryl)imide compound as the invention of the present application is not known.

REFERENCES ABOUT PRIOR ART

Patent Publication

Patent Publication 1: U.S. Pat. No. 3,379,509
Patent Publication 2: U.S. Pat. No. 4,315,935
Patent Publication 3: International Application Publication 2007/022624

Non-Patent Publication

Non-Patent Publication 1: Inorganic Chemistry, 37 (24), pages 6295-6303 (1998)

Non-Patent Publication 2: Inorganic Synthesis, 11, pages 138-143 (1968)
Non-Patent Publication 3: Inorganic Chemistry Communications, 2 (6), pages 261-264 (1999)
Non-Patent Publication 4: Z. Anorg. Allg. Chem. 412 (1), pages 65-70 (1975)
Non-Patent Publication 5: Ind. Eng. Chem. pages 751-753 (1943)
Non-Patent Publication 6: Ber., 56, B, 1656 (1923)

SUMMARY OF THE INVENTION

The method of Patent Publication 1 is hard to adopt as an industrial production method, from the fact that fluorosulfonic acid which is highly toxic and corrosive is used therein and that bis(fluorosulfonyl)imide and fluorosulfonic acid obtained through this reaction are so difficult to separate as to lower the yield. Additionally, in the methods of Non-Patent Publications 1 and 2, costly and highly toxic arsenic trifluoride and antimony trifluoride are used, so that it is not advantageous to apply these methods to an industrial mass production.

Furthermore, the methods of Patent Publication 2 and Non-Patent Publication 3 have a disadvantage of using relatively costly chlorosulfonylisocyanate ($ClSO_2NCO$) or N-sulfonyl trichlorophosphazene ($ClSO_2NPCl_3$). The methods of Patent Publication 3 and Non-Patent Publication 4 use a costly silazane derivative for a nitrogen source and therefore not said to be an inexpensive method.

Thus, the conventionally known methods for producing a bis(halogenated sulfonyl)imide compound which is useful as an intermediate for medicines and agrichemicals, a battery electrolyte or an acid catalyst are not sufficiently satisfactory as a large-scale production method, though suitable for obtaining a target substance on a small scale.

In view of the above objects, the present inventors had eagerly made studies thereon. As a result, the inventors have found a method for producing "a salt or a complex comprising imide and an organic base" represented by the formula [1]

[1]

[In the formula [1], R represents a halosulfonyl group ($—SO_2X^1$ where $X^1$ is a halogen such as fluorine, chlorine, bromine and iodine) or dihalophosphoryl group ($—POX^2X^3$ where $X^2$ and $X^3$ are identical or different halogens, such as fluorine, chlorine, bromine and iodine). B represents an organic base.] at a high selectivity and a high yield, the method being characterized by reacting a halogenated sulfuryl ($SO_2X^4X^5$ where $X^4$ and $X^5$ represent identical or different halogens, such as fluorine, chlorine, bromine and iodine and identical to or different from the above-mentioned $X^1$) or halogenated phosphoryl ($P(=O)X^6X^7X^8$ where $X^6$, $X^7$ and $X^8$ represent identical or different halogens, such as fluorine, chlorine, bromine and iodine and identical to or different from the above-mentioned $X^2$ or $X^3$) with ammonia in the presence of an organic base. With this, the present invention had been accomplished.

More specifically, inventions discussed in the following [Invention 1] to [Invention 9] are provided.

[Invention 1]
A method for producing "a salt or a complex comprising imide and an organic base" represented by the formula [1], comprising the step of:

reacting a halogenated sulfuryl or halogenated phosphoryl with ammonia in the presence of an organic base.

[Invention 2]

A method for producing "a salt or a complex comprising imide and an organic base" represented by the formula [1], comprising the step of:

reacting a halogenated sulfuryl with ammonia in the presence of an organic base.

[Invention 3]

A method as discussed in Invention 1, further comprising the step of:

bringing ammonia into the reaction, after making the organic base and the halogenated sulfuryl or the halogenated phosphoryl coexistent in the reaction system.

[Invention 4]

A method as discussed in Invention 1, wherein the organic base is a tertiary amine represented by the formula [2]

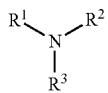

[2]

[where $R^1$, $R^2$ and $R^3$ are identical or different and represent a linear or branched alkyl group having 1 to 6 carbon atoms, a cycloalkyl group having 3 to 8 carbon atoms, or an aryl group (a part or all of hydrogen atoms of the aryl group may be substituted with halogen (fluorine, chlorine, bromine or iodine), an alkyl group having 1 to 10 carbon atoms, a haloalkyl group having 1 to 10 carbon atoms, a cycloalkyl group having 3 to 8 carbon atoms, amino group, nitro group, acetyl group, cyano group or hydroxyl group)], a nitrogen-containing heteroaromatic compound, or a compound having an imine framework as follows:

—C=N—C—.

[Invention 5]

A method as discussed in Invention 1, wherein the organic base is trimethylamine, triethylamine, diisopropylethylamine, tri-n-propylamine, tributylamine or pyridine.

[Invention 6]

A method as discussed in Invention 1, wherein the organic base is in an amount of 1 to 50 moles relative to 1 mole of ammonia.

[Invention 7]

A method as discussed in Invention 1, wherein the halogenated sulfuryl or halogenated phosphoryl is used in an amount of 1 to 10 moles relative to 1 mole of ammonia.

[Invention 8]

A method as discussed in Invention 1, wherein the halogenated sulfuryl or halogenated phosphoryl is reacted with ammonia in the presence of the organic base at a reaction temperature of −50 to 150° C.

[Invention 9]

A method for producing an imide metal salt represented by the formula [3]

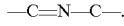

[3]

[where R represents a halosulfonyl group (—$SO_2X^1$ where $X^1$ is a halogen such as fluorine, chlorine, bromine and iodine) or dihalophosphoryl group (—$POX^2X^3$ where $X^2$ and $X^3$ are identical or different halogens, such as fluorine, chlorine, bromine and iodine), M represents an alkali metal or alkaline earth metal, and n represents an integer identical to the valence of the metal], comprising the step of:

reacting "the salt or the complex comprising imide and the organic base" obtained by the method as discussed in Invention 1 with a hydroxide or carbonate of alkali metal or a hydroxide or carbonate of alkaline earth metal.

The invention of the present application is characterized by "reacting halogenated sulfuryl or halogenated phosphoryl with ammonia in the presence of an organic base". As discussed in Non-Patent Publications 5 and 6, it is traditionally known that a compound referred to as "sulfamide" is formed when halogenated sulfuryl is reacted with anhydrous ammonia. Moreover, these publications also disclose that many other by-products are formed in addition to sulfamide (see Scheme 1).

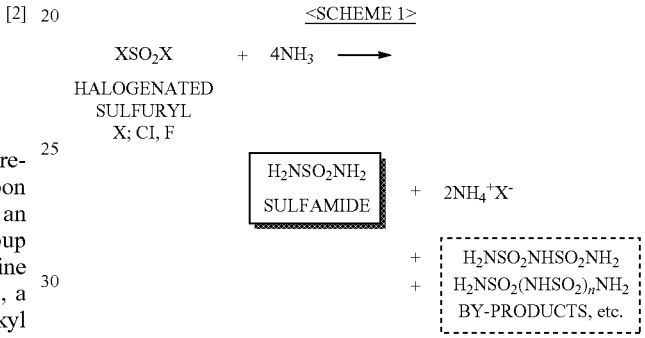

<SCHEME 1>

On the other hand, Patent Publication 3 discloses that halogenated sulfuryl is reacted with amine such as a silazane derivative thereby producing a corresponding imide compound. If the method of Patent Publication 3 is applied to the invention of the present application and, for example, sulfuryl fluoride ($SO_2F_2$) is used therein, however, it has been found that the target substance "a salt or a complex comprising bisfluorosulfonylimide and an organic base" is hardly obtained and by-products including sulfamide are greatly formed (see the following Scheme 2).

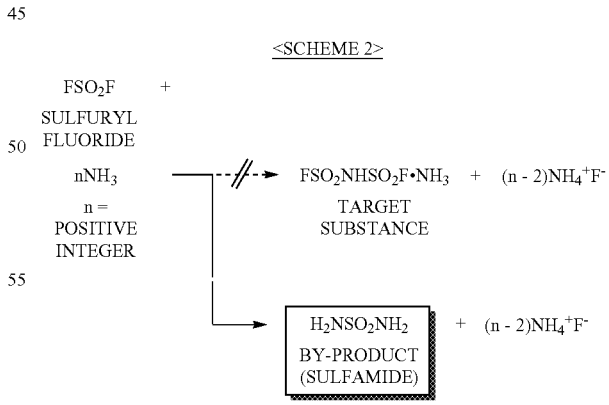

<SCHEME 2>

In view of the above, the present inventors brought an organic base into coexistence with the ammonia in the reaction system, thereby finding that sulfamide was hardly formed and "a salt or a complex comprising imide and an organic base" was formed at a high conversion rate and a high selectivity (see the following Scheme 3).

<SCHEME 3>

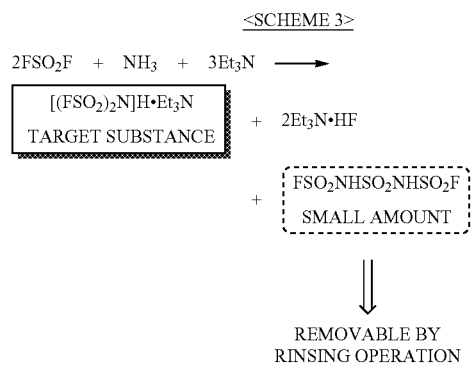

REMOVABLE BY
RINSING OPERATION

<SCHEME 4>

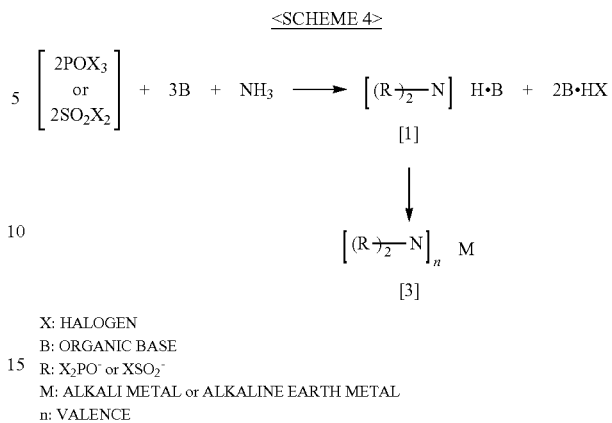

X: HALOGEN
B: ORGANIC BASE
R: $X_2PO^-$ or $XSO_2^-$
M: ALKALI METAL or ALKALINE EARTH METAL
n: VALENCE

By the way, the target substance "a salt or a complex comprising bisfluorosulfonylimide and an organic base" is a compound slightly soluble in water, in itself. Accordingly, even if a small amount of the following by-product $FSO_2NHSO_2NHSO_2F$ is sometimes formed, the by-product can be fully removed by a convenient and facile rinsing operation.

Moreover, the present inventors found a preferable condition for carrying out the invention of the present application in regard to a method of introducing a reagent into the reaction system. By employing such an operation as to modify the order of addition to the reaction system, i.e., a method where ammonia is introduced into the reaction system after the addition of an inorganic base and sulfuryl fluoride to the system, the target substance is obtained at a high selectivity and a high yield. This is an extremely useful finding.

The present inventors further found that a bis(halogenated sulfonyl)imide metal salt represented by the formula [3] can be easily obtained by reacting "a salt or a complex comprising bis(halogenated sulfonyl)imide and an organic base" with an alkali metal hydroxide or an alkaline earth metal hydroxide.

Thus, the present invention suitably employs a preferable reaction condition in producing an imide compound, thereby allowing an industrially easy production as compared with conventional techniques.

DETAILED DESCRIPTION

The present invention employs halogenated sulfuryl or halogenated phosphoryl, which is not only inexpensive but also favorable to handling in large quantity. With this, there is provided the effect of producing a target imide derivative at a high yield while greatly suppressing the formation of by-products.

Hereinafter, the present invention will be discussed in detail. The present invention is a method for producing "a salt or a complex comprising imide and an organic base" represented by the formula [1], characterized by reacting a halogenated sulfuryl or halogenated phosphoryl with ammonia in the presence of an organic base.

Then, the invention is summarized in the following Scheme 4, including a production method of reacting the obtained "salt or complex comprising imide and the organic base" with a hydroxide or carbonate of alkali metal or a hydroxide or carbonate of alkaline earth metal thereby obtaining a bisfluorosulfonylimide metal salt represented by the formula [3].

A halogenated sulfuryl used in the present invention is exemplified by sulfuryl fluoride, sulfuryl chloride, sulfuryl bromide and sulfuryl iodide, while a halogenated phosphoryl is exemplified by phosphoryl fluoride, phosphoryl chloride, phosphoryl bromide and phosphoryl iodide. Among these, the particularly preferable are sulfuryl fluoride, sulfuryl chloride, phosphoryl fluoride and phosphoryl chloride.

The amount of a halogenated sulfuryl or halogenated phosphoryl is usually 1 to 10 moles, preferably 1 to 8 moles and more preferably 1 to 5 moles relative to 1 mole of ammonia.

An organic base used in the present invention is a tertiary amine represented by the formula [2], a nitrogen-containing heteroaromatic compound, or a compound having an imine framework as follows:

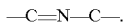

Concrete examples of each of the compounds will be hereinafter discussed.

(a) Tertiary Amine:
trimethylamine, triethylamine, N-ethyldiisopropylamine, tri-n-propylamine, triisopropylamine, tri-n-butylamine, trioctylamine, tridecylamine, triphenylamine, tribenzylamine, tris(2-ethylhexyl)amine, N,N-dimethyldecylamine, N-benzyldimethylamine, N-butyldimethylamine, N,N-dimethylcyclohexylamine, N,N,N',N'-tetramethylethylenediamine, N,N-dimethylaniline, 1,4-diazabicyclo[2.2.2]octane, N-methylpyrrolidine, N-methylpiperidine, N-methylmorpholine, N-ethylmorpholine, N,N'-dimethylpiperazine, N-methylpipecoline, N-methylpyrrolidone, N-vinyl-pyrrolidone, bis(2-dimethylamino-ethyl)ether, N,N,N,N',N"-pentamethyldiethylenetriamine, triethanolamine, tripropanolamine, dimethylethanolamine, dimethylaminoethoxyethanol, N,N-dimethylaminopropylamine, N,N,N',N',N"-pentamethyldipropylenetriamine, tris(3-dimethylaminopropyl)amine, tetramethylimino-bis(propylamine), N-diethyl-ethanolamine, etc.

(b) Nitrogen-Containing Heteroaromatic Compound:
pyridine, 2,4,6-trimethylpyridine, 4-dimethylaminopyridine, lutidine, pyrimidine, pyridazine, pyrazine, oxazole, isoxazole, thiazole, isothiazole, imidazole, 1,2-dimethylimidazole, 3-(dimethylamino)propylimidazole, pyrazole, furazan, pyrazine, quinoline, isoquinoline, purine, 1H-indazole, quinazoline, cinnoline, quinoxaline, phthalazine, pteridine, phenanthridine, 2,6-di-t-butylpyridine, 2,2'-bipyridine, 4,4'-dimethyl-2,2'-bipyridyl, 4,4'-dimethyl-2,2'-bipyridyl, 5,5'-dimethyl-2,2'-bipyridyl, 6,6'-t-butyl-2,2'-dipyridyl, 4,4'-diphenyl-2,2'-bipyridyl, 1,10-phenanthroline, 2,7-dimethyl-1,10-phenanthroline, 5,6-dimethyl-1,10-phenanthroline, 4,7-diphenyl-1,10-phenanthroline, etc.

(c) Imine-Based Base:

1,8-diazabicyclo[5.4.0]undec-7-ene, 1,5-diazabicyclo[4.3.0]non-5-ene, etc.

Among these, the preferable are tertiary amines such as trimethylamine, triethylamine, diisopropylethylamine, tripropylamine, tributylamine and the like, secondary amines such as diisopropylamine and the like, and nitrogen-containing heteroaromatic compounds such as pyridine, 2,3-lutidine, 2,4-lutidine, 2,6-lutidine, 3,4-lutidine, 3,5-lutidine, 2,4,6-collidine, 3,5,6-collidine and the like. The further preferable are trimethylamine, triethylamine, diisopropylethylamine, tripropylamine, tributylamine, pyridine and the like.

Stoichiometrically, the amount of the organic base to be used is 3 moles relative to 1 mole of ammonia while being 1.5 moles relative to 1 mole of halogenated sulfuryl or halogenated phosphoryl. However, the organic base is preferably used in larger amount than stoichiometric ones in order to develop the reaction smoothly, as shown in the above-mentioned scheme.

The amount of the organic base to be used is therefore 1 to 50 moles (preferably 1 to 10 moles) relative to 1 mole of ammonia while being 1.5 to 10 moles (preferably 2 to 5 moles) relative to 1 the sulfuryl or phosphoryl.

The reaction in itself can proceed even in a case where the organic base is less than 1.5 moles relative to 1 the sulfuryl or phosphoryl. In this case, however, the ratio of ammonia in the reaction system is to be so large that a great amount of sulfamide is produced and the conversion rate is sometimes reduced. Therefore, it is preferable to perform the reaction with the above-mentioned equivalent amount of organic base.

Additionally, the present invention allows the reaction to proceed in the coexistence with an organic solvent or water. The organic solvent means an inactive organic compound which does not directly relate to the reaction of the present invention. The reaction solvent is exemplified by: aliphatic hydrocarbons such as n-hexane, cyclohexane and n-heptane; aromatic hydrocarbons such as benzene, toluene, xylene and mesitylene; halogenated hydrocarbons such as methylene chloride, chloroform and 1,2-dichloroethane; ethers such as diethyl ether, tetrahydrofuran and tert-butyl methyl ether; esters such as ethyl acetate and butyl acetate; amides such as N,N-dimethylformamide, N,N-dimethylacetamide and N-methylpyrrolidone; nitriles such as acetonitrile and propionitrile; dimethylsulfoxide; and the like.

Among these, the preferable are esters such as ethyl acetate and butyl acetate, amides such as N,N-dimethylformamide, N,N-dimethylacetamide and N-methylpyrrolidone, nitriles such as acetonitrile and propionitrile, and dimethylsulfoxide. The further preferable are nitriles such as acetonitrile and propionitrile. These reaction solvents may be used singly or in combination.

Though not particularly limited, the amount of the organic solvent or water to be used is required only to be not smaller than 0.1 L (liter), usually preferably 0.1 to 20 L and particularly preferably 0.1 to 10 L.

Incidentally, in the case where the organic base is in the liquid form (for example, triethylamine or the like), it serves also as a solvent. Therefore, such an organic base may excessively be used in order to let it function as a solvent.

The temperature condition is not particularly limited and is required only to be within a range of from −50 to 150° C. It is usually preferably −20 to 100° C. and particularly preferably −10 to 70° C. Temperatures of lower than −50° C. reduce the reaction rate, while those exceeding 150° C. sometimes cause the decomposition of products and the like.

The pressure condition is not particularly limited and therefore it is possible to conduct the reaction under the condition of atmospheric pressure (0.1 MPa (an absolute pressure which will be adhered to hereinafter)) or under a depressurized or pressurized condition provided in the use of a pressure-resistant reactor. More specifically, the reaction is required only to be conducted within a range of from 0.01 to 2 MPa, preferably 0.01 to 1.5 MPa, and more preferably 0.1 to 1 MPa.

A reactor to be used in the reaction is exemplified by Monel, Hastelloy, nickel, and pressure-resistant reactors subjected to lining with these metals or fluorocarbon polymers such as polytetrafluoroethylene and perfluoropolyether resin.

The reaction time is not particularly limited and required only to be within a range of from 0.1 to 48 hours. The reaction time differs according to the substrate and the reaction conditions, so that it is preferable to pursue the progress of the reaction by using an analytical means such as gas chromatography, liquid chromatography and NMR thereby determining a temporal point at which the raw material has been consumed off as the endpoint of the reaction.

Hereinafter, "preferable conditions" in the present invention will be discussed.

"A salt or a complex comprising imide and an organic base" represented by the formula [1] is obtained by reacting halogenated sulfuryl or halogenated phosphoryl with ammonia in the presence of an organic base. Concerning the order in which materials are charged into the reactor, it is preferable, for example, to charge a pressure-resistant reactor such as an autoclave with an organic solvent, the organic base and halogenated sulfuryl or halogenated phosphoryl and then with ammonia, followed by causing a reaction with the reactor closed tightly. At the time of the reaction, it is preferable that the halogenated sulfuryl or halogenated phosphoryl is in an amount of 2 to 5 moles and the organic base is in an amount of 3 to 10 moles, relative to 1 mole of ammonia.

Furthermore, the amount of the organic solvent to be used is preferably 0.1 to 20 L relative to 1 mole of ammonia. The temperature condition is preferably 0 to 100° C. Moreover, the pressure condition is preferably 0.1 to 1.5 MPa.

By conducting the reaction under such conditions, it becomes possible to obtain "a salt or a complex comprising imide and an organic base" at a high selectivity.

By the way, the target substance "a salt or a complex comprising imide and an organic base" is a compound insoluble in water, in itself. Though a small amount of the following by-product

is sometimes formed in the reaction system, it is therefore possible to remove the by-product by a convenient and facile operation (such as rinsing with water). An operation in which rinsing with water is performed as will be discussed in Examples of the present application is one of the favorable embodiments, in terms of improvement of the chemical purity of the target substance "a salt or a complex comprising imide and an organic base".

Then, there will be discussed a method for reaction the obtained "salt or complex comprising imide and the organic base" with a hydroxide or carbonate of alkali metal or a hydroxide or carbonate of alkaline earth metal thereby obtaining a bishalogenated sulfonylimide metal salt represented by the formula [3].

The hydroxide of alkali metal is exemplified by lithium hydroxide (LiOH), potassium hydroxide (KOH), rubidium hydroxide (RbOH), and cesium hydroxide (CsOH). The carbonate of alkali metal is exemplified by lithium carbonate ($Li_2CO_3$), potassium carbonate ($K_2CO_3$), rubidium carbonate ($Rb_2CO_3$), and cesium carbonate ($Cs_2CO_3$). The hydroxide of alkaline earth metal is exemplified by magnesium hydroxide ($Mg(OH)_2$), calcium hydroxide ($Ca(OH)_2$), barium hydroxide ($Ba(OH)_2$), and strontium hydroxide ($Sr(OH)_2$). The carbonate of alkaline earth metal is exemplified by magnesium carbonate ($MgCO_3$), calcium carbonate ($CaCO_3$), barium carbonate ($BaCO_3$), and strontium carbonate ($SrCO_3$). Preferable examples are lithium hydroxide (LiOH), potassium hydroxide (KOH), rubidium hydroxide (RbOH), cesium hydroxide (CsOH), magnesium hydroxide ($Mg(OH)_2$), calcium hydroxide ($Ca(OH)_2$), barium hydroxide ($Ba(OH)_2$), and strontium hydroxide ($Sr(OH)_2$). In addition, these hydroxides and carbonates of alkali metal and of alkaline earth metal may be used singly or in combination of not less than two kinds thereof. In the case of using two kinds or more, it is preferable to use a combination of hydroxide and carbonate of the same alkali metal (e.g. potassium hydroxide and potassium carbonate) or a combination of hydroxide and carbonate of the same alkaline earth metal (e.g. magnesium hydroxide and magnesium carbonate).

The amount of a hydroxide or carbonate of alkali metal or a hydroxide or carbonate of alkaline earth metal to be used is preferably 1 to 5 moles, and more preferably 1 to 3 moles relative to 1 mole of "a salt or a complex comprising imide and an organic base". The reaction is to proceed even when using an amount exceeding 5 moles or when using an excessive amount of base; however, by which "a salt or a complex comprising imide and an organic base" is sometimes decomposed so as to reduce the yield. Therefore it is not preferable to use an excessive amount of base. Additionally, an amount smaller than 1 mole is not preferable either, because it reduces the conversion rate.

At the time of bringing a hydroxide or carbonate of alkali metal or a hydroxide or carbonate of alkaline earth metal into reaction, a solvent may be used. For example, in the case of using water as the solvent, it is preferable to add water in such a manner that the concentration of the base becomes 10 to 70 mass % in general, preferably 20 to 60 mass % and more preferably 30 to 60 mass %. An excessively small amount of water makes stirring difficult in the reaction system. Further, when water has an excessively large amount, treatments performed after the reaction are made complicated and additionally a reactor bigger than usual is needed.

Incidentally, it is one of favorable embodiments to add an aqueous solution of potassium hydroxide in the concentration of 48 mass % in Examples of the present application.

Moreover, an organic solvent other than water is also acceptable, in which a solvent such as ethers including diethyl ether, dioxane, tetrahydrofuran and ethylene glycol dimethyl ether may be used. Additionally, these may be used in combination with water. The amount of the solvent to be used is suitably selected usually from a range of from 0.5 to 10 times, preferably from a range of from 1 to 7 times as much as the volume of "a salt or a complex comprising imide and an organic base". However, there is little merit in using an organic solvent other than water since the reaction proceeds sufficiently even in the case of using water.

The reaction temperature is not particularly limited but usually −10 to 110° C., preferably 25 to 80° C. When the reaction temperature is lower than −10° C., the reaction cannot proceed sufficiently, which causes a yield reduction and economical disadvantage. Alternatively, there may arise a problem, for example, of reducing the reaction rate so as to need a long period of time for terminating the reaction. On the other hand, when the reaction temperature exceeds 110° C., by-products are easily formed. Additionally, excessive heating is not good for energy efficiency.

The reaction time is not particularly limited and required only to be within 24 hours in general. It is preferable to pursue the progress of the reaction by using an analytical means such as ion chromatography and NMR thereby determining a temporal point at which the raw material has been consumed off as the endpoint of the reaction.

As a reactor to be used in the present step, it is possible to cite reactors which can accept a reaction under atmospheric pressure or applied pressure. It is exemplified by: containers formed of metal such as stainless steel, Hastelloy and Monel; and reactors formed of tetrafluoroethylene resin, chlorotrifluoroethylene resin, vinylidene fluoride resin, PFA resin, polypropylene resin, polyethylene resin, glass or the like and subjected to lining at its inner section.

EXAMPLES

The present invention will be more specifically discussed with reference to the following Examples; however, the present invention is not limited by these Examples. In the following description, "%" used for compositional analysis means "mol %" of the composition obtained by analyzing a reaction mixture by nuclear magnetic resonance (NMR) unless otherwise specified.

Example 1

A 1 L autoclave was charged with 184 g of acetonitrile and 184 g (1.82 mol) of triethylamine and then cooled to 5° C. with ice water, followed by charging 153 g (1.50 mol) of sulfuryl fluoride thereinto. Subsequent to the introduction of sulfuryl fluoride, 9.1 g (0.53 mol) of anhydrous ammonia was charged thereinto with spending one hour. Thereafter, the reactor was increased in temperature to room temperature, followed by stirring for 48 hours. The production rate in this reaction was 99.2%, while 0.8% of $FSO_2NHSO_2NHSO_2F$ was produced. A solvent was distilled out of the reaction liquid, and then ether and water were added to the residue, followed by extraction and rinsing. Subsequently, an organic layer was separated and a solvent was distilled out thereof, thereby obtaining 128 g of a bisfluorosulfonylimide triethylammonium salt (incidentally, the ammonium salt was brought into a subsequent reaction as it was without being subjected to isolation and purification).

Then, the ammonium salt was mixed with an aqueous solution containing 25.2 g of potassium hydroxide, while spending one hour at room temperature. Thereafter triethylamine and water were distilled out of a reaction mixture thereby obtaining potassium bisfluorosulfonylimide. Acetonitrile was added thereto and then an undissolved component was separated. Acetonitrile was distilled off, thereby obtaining 96.2 g of potassium bisfluorosulfonylimide having a purity of 99% or more. The yield was 83%.

Example 2

A 1 L autoclave was charged with 384 g of acetonitrile and 158 g (2.00 mol) of pyridine and then cooled to 5° C. with ice water, followed by charging 132 g (1.29 mol) of sulfuryl fluoride thereinto. Subsequent to the introduction of sulfuryl fluoride, 9.8 g (0.58 mol) of anhydrous ammonia was charged thereinto with spending one hour. Thereafter, the reactor was increased in temperature to room temperature, followed by stirring for 48 hours. The production rate in this reaction was 99.0%, while 1.0% of $FSO_2NHSO_2NHSO_2F$ was produced. A solvent was distilled out of the reaction liquid, and then ether and water were added to the residue, followed by extraction and rinsing. Subsequently, an organic layer was separated and a solvent was distilled out thereof, thereby obtaining 127 g of a bisfluorosulfonylimide pyridine salt (incidentally, the pyridine salt was brought into a subsequent reaction as it was without being subjected to isolation and purification).

Then, the pyridine salt was mixed with an aqueous solution containing 11.6 g of lithium hydroxide, while spending one hour at room temperature. After mixing, a procedure of Example 1 was repeated, thereby obtaining 86.3 g of lithium bisfluorosulfonylimide having a purity of 99% or more. The yield was 81%.

Example 3

A 200 mL autoclave was charged with 45.0 g of acetonitrile and 45.0 g (445 mmol) of pyridine and then cooled to 5° C. with ice water, followed by charging 2.4 g (140 mmol) of anhydrous ammonia was charged thereinto. Thereafter, 28.7 g (286 mmol) of sulfuryl fluoride was introduced into the reactor. The reactor was increased in temperature to room temperature, followed by stirring for 24 hours. The production rate in this reaction was 70.2%, while 29.8% of $FSO_2NHSO_2NHSO_2F$ was produced. A solvent was distilled out of the reaction liquid, and then ether and water were added to the residue, followed by extraction and rinsing. Subsequently, an organic layer was separated and a solvent was distilled out thereof, thereby obtaining 13.3 g of a bisfluorosulfonylimide triethylammonium salt (incidentally, the ammonium salt was brought into a subsequent reaction as it was without being subjected to isolation and purification).

Then, the ammonium salt was mixed with an aqueous solution containing 2.7 g of potassium hydroxide. After mixing, a procedure of Example 1 was repeated, thereby obtaining 9.9 g of potassium bisfluorosulfonylimide. The yield was 32%.

Example 4

A 200 mL autoclave was charged with 105 g of acetonitrile and 21.2 g (210 mmol) of triethylamine and then cooled to 5° C. with ice water, followed by charging 1.2 g (70 mmol) of anhydrous ammonia was charged thereinto. Thereafter, 15.5 g (152 mmol) of sulfuryl fluoride was introduced into the reactor. The reactor was increased in temperature to room temperature, followed by stirring for 12 hours. The production rate in this reaction was 82.3%, while 17.7% of $FSO_2NHSO_2NHSO_2F$ was produced. A solvent was distilled out of the reaction liquid, and then ether and water were added to the residue, followed by extraction and rinsing. Subsequently, an organic layer was separated and a solvent was distilled out thereof, thereby obtaining 13.0 g of a bisfluorosulfonylimide triethylammonium salt (incidentally, the ammonium salt was brought into a subsequent reaction as it was without being subjected to isolation and purification).

Then, the ammonium salt was mixed with an aqueous solution containing 2.6 g of potassium hydroxide, while spending one hour at room temperature. After mixing, a procedure of Example 1 was repeated, thereby obtaining 9.6 g of potassium bisfluorosulfonylimide. The purity was 99% or more and the yield was 63%.

By adding the organic solvent in a greater amount than that in Example 3, the yield can be further improved.

Example 5

A 1 L autoclave was charged with 200 g of acetonitrile and 200 g (1.97 mol) of triethylamine and then cooled to 5° C. with ice water, followed by charging 202 g (1.50 mol) of sulfuryl chloride was charged thereinto. Subsequent to the introduction of sulfuryl fluoride, 8.5 g (0.50 mol) of anhydrous ammonia was charged thereinto with spending one hour. The reactor was increased in temperature to room temperature, followed by stirring for 48 hours. A solvent was distilled out of the reaction liquid, and then ether and water were added to the residue, followed by extraction and rinsing. Subsequently, an organic layer was separated and a solvent was distilled out thereof, thereby obtaining 126 g of a bis(chlorosulfonyl)imide triethylammonium salt (incidentally, the ammonium salt was brought into a subsequent reaction as it was without being subjected to isolation and purification).

Then, the ammonium salt was mixed with an aqueous solution containing 22.4 g of potassium hydroxide, while spending one hour at room temperature. Triethylamine and water were distilled out of the reaction mixture thereby obtaining potassium bis(chlorosulfonyl)imide. Acetonitrile was added thereto and then an undissolved component was separated. Acetonitrile was distilled off, thereby obtaining 79.6 g of potassium bis(chlorosulfonyl)imide having a purity of 99% or more. The yield was 79%.

Example 6

A 1 L autoclave was charged with 210 g of acetonitrile and 210 g (2.08 mol) of triethylamine and then cooled to 5° C. with ice water, followed by charging 155 g (1.56 mol) of phosphoryl fluoride was charged thereinto. Subsequently, 10.4 g (0.61 mol) of anhydrous ammonia was charged thereinto with spending one hour. The reactor was increased in temperature to room temperature, followed by stirring for 48 hours. The production rate in this reaction was such that the production of potassium bis(chlorosulfonyl)imide was 100% and that the production of F2P(=O)NPF(=O)NP(=O)F2 could not be confirmed.

Example 7

A 1 L autoclave was charged with 210 g of acetonitrile and 210 g (0.71 mol) of triethylamine and then cooled to 5° C. with ice water, followed by charging 57.4 g (0.374 mol) of phosphoryl fluoride was charged thereinto. Subsequently, 3.0 g (0.176 mol) of anhydrous ammonia was introduced thereinto with spending one hour. The reactor was increased in temperature to room temperature, followed by stirring for 48 hours. The production rate in this reaction was such that the production of bis(dichlorophosphoryl)imide was 98% and a remaining 2% was occupied by an intermediate, i.e., chlorophosphorylamide.

Comparative Example 1

A 200 mL autoclave was charged with 50 g of acetonitrile and then cooled to 5° C. with ice water, followed by charging 12.4 g (729 mol) of anhydrous ammonia thereinto. Subsequently, 23.3 g (228 mmol) of sulfuryl fluoride was introduced thereinto. The reactor was increased in temperature to room temperature, followed by stirring for 48 hours. This reaction liquid was filtered and a solvent was distilled out thereof, thereby obtaining 10.1 g of a white solid. The primary component of the white solid was confirmed to be sulfamide ($H_2NSO_2NH_2$). Additionally, it was confirmed that the white solid contained 3 wt % of fluorosulfonylamide ($FSO_2NH_2$) while containing a scant 0.3 wt % of a bisfluorosulfonylimide ammonium salt (Yield: 0.1%).

It is apparent from this that a target ammonium salt is hardly obtained in the absence of the organic base.

Comparative Example 2

A 200 mL autoclave was charged with 50 g of acetonitrile and then cooled to 5° C. with ice water, followed by charging 27.0 g (200 mmol) of sulfuryl chloride thereinto. Subsequently, 12.0 g (705 mmol) of anhydrous ammonia was introduced thereinto. The reactor was increased in temperature to room temperature, followed by stirring for 48 hours. This reaction liquid was filtered and a solvent was distilled out thereof, thereby obtaining 9.8 g of a white solid. The primary component of the white solid was confirmed to be sulfamide ($H_2NSO_2NH_2$). Additionally, it was confirmed that the white solid did not contain a bis(chlorosulfonyl)imide ammonium salt.

It is thus apparent that a target ammonium salt is hardly obtained in the absence of the organic base.

The invention claimed is:

1. A method for producing a salt or a complex comprising imide and an organic base represented by the formula [1]

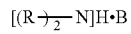 [1]

where R represents a halosulfonyl group (—$SO_2X^1$ where $X^1$ is a halogen) or dihalophosphoryl group (—$POX^2X^3$ where $X^2$ and $X^3$ are identical or different halogens) and B represents an organic base, comprising the step of:

reacting a dihalogenated sulfuryl ($SO_2X^4X^5$ where $X^4$ and $X^5$ represent identical or different halogens and identical to or different from the above-mentioned $X^1$) or halogenated phosphoryl (P(=O)$X^6X^7X^8$ where $X^6$, $X^7$ and $X^8$ represent identical or different halogens and identical to or different from the above-mentioned $X^2$ or $X^3$) with ammonia in the presence of an organic base, wherein the ammonia is brought into the reaction after the organic base and the dihalogenated sulfuryl or the halogenated phosphoryl are made firstly coexistent in the reaction system.

2. A method for producing a salt or a complex comprising imide and an organic base represented by the formula [1]

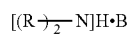 [1]

where R represents a halosulfonyl group (—$SO_2X^1$ where $X^1$ is a halogen) or dihalophosphoryl group (—$POX^2X^3$ where $X^2$ and $X^3$ are identical or different halogens) and B represents an organic base, comprising the step of:

reacting a dihalogenated sulfuryl ($SO_2X^4X^5$ where $X^4$ and $X^5$ represent identical or different halogens and identical to or different from the above-mentioned $X^1$) with ammonia in the presence of an organic base, wherein the ammonia is brought into the reaction after the organic base and the dihalogenated sulfuryl are made firstly coexistent in the reaction system.

3. A method as claimed in claim 1, wherein the organic base is a tertiary amine represented by the formula [2]

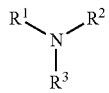 [2]

where $R^1$, $R^2$ and $R^3$ are identical or different and represent a linear or branched alkyl group having 1 to 6 carbon atoms, a cycloalkyl group having 3 to 8 carbon atoms, or an aryl group (a part or all of hydrogen atoms of the aryl group may be substituted with halogen, an alkyl group having 1 to 10 carbon atoms, a haloalkyl group having 1 to 10 carbon atoms, a cycloalkyl group having 3 to 8 carbon atoms, amino group, nitro group, acetyl group, cyano group or hydroxyl group), a nitrogen-containing heteroaromatic compound, or a compound having an imine framework as follows:

—C=N—C—.

4. A method as claimed in claim 1, wherein the organic base is trimethylamine, triethylamine, diisopropylethylamine, tri-n-propylamine, tributylamine or pyridine.

5. A method as claimed in claim 1, wherein the organic base is in an amount of 1 to 50 moles relative to 1 mole of ammonia.

6. A method as claimed in claim 1, wherein the dihalogenated sulfuryl or halogenated phosphoryl is used in an amount of 1 to 10 moles relative to 1 mole of ammonia.

7. A method as claimed in claim 1, wherein the dihalogenated sulfuryl or halogenated phosphoryl is reacted with ammonia in the presence of the organic base at a reaction temperature of −50 to 150° C.

8. A method for producing an imide metal salt represented by the formula [3]

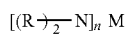 [3]

where R represents a halosulfonyl group (—$SO_2X^1$ where $X^1$ is a halogen) or dihalophosphoryl group (—$POX^2X^3$ where $X^2$ and $X^3$ are identical or different halogens) M represents an alkali metal or alkaline earth metal, and n represents an integer identical to the valence of the metal, comprising the steps of:

(a) reacting a dihalogenated sulfuryl ($SO_2X^4X^5$ where $X^4$ and $X^5$ represent identical or different halogens and identical to or different from the above-mentioned $X^1$) or halogenated phosphoryl (P(=O)$X^6X^7X^8$ where $X^6$, $X^7$ and $X^8$ represent identical or different halogens and identical to or different from the above-mentioned $X^2$ or $X^3$) with ammonia in the presence of an organic base, wherein the ammonia is brought into the reaction after the organic base and the dihalogenated sulfuryl or the halogenated phosphoryl are made firstly coexistent in the reaction system, thereby producing a salt or a complex comprising imide and an organic base represented by the formula [1]

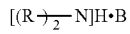 [1]

where B represents the organic base; and (b) reacting the salt or the complex comprising imide and the organic base with a hydroxide or carbonate of alkali metal or a hydroxide or carbonate of alkaline earth metal.

\* \* \* \* \*